United States Patent [19]
Kovacevic

[11] Patent Number: 5,317,916
[45] Date of Patent: Jun. 7, 1994

[54] DIGIT GRIP SENSOR

[75] Inventor: Nebojsa Kovacevic, Plymouth, Minn.

[73] Assignee: N.K. Biotechnical Engineering Company, Minneapolis, Minn.

[21] Appl. No.: 935,030

[22] Filed: Aug. 25, 1992

[51] Int. Cl.[5] .......................................... A63B 21/02
[52] U.S. Cl. ........................ 73/379.03; 73/862.635; 482/49
[58] Field of Search ......... 73/379.02, 379.03, 862.632, 73/862.635, 862.541; 482/47, 49, 50

[56] References Cited

U.S. PATENT DOCUMENTS

| | | | |
|---|---|---|---|
| 2,814,491 | 11/1957 | Proctor | 482/50 |
| 3,442,132 | 5/1969 | Demare | 73/379.03 |
| 3,672,219 | 6/1972 | Van Patten | 73/379 |
| 3,696,317 | 10/1972 | Farr | 73/862.632 X |
| 3,738,651 | 6/1973 | Norman et al. | 272/67 |
| 3,848,468 | 11/1974 | Richards | 73/379.02 |
| 3,871,216 | 3/1975 | Eder | 73/862.635 |
| 4,553,746 | 11/1985 | Lee | 73/379.03 |
| 4,674,330 | 6/1987 | Ellis | 73/379.03 |
| 5,125,878 | 6/1992 | Wingate et al. | 482/49 |
| 5,147,256 | 9/1992 | Silagy | 482/47 |
| 5,157,970 | 10/1992 | Lewis, Jr. | 73/379.02 |

FOREIGN PATENT DOCUMENTS 2153540 8/1985 United Kingdom .......... 73/379.02

OTHER PUBLICATIONS

The Journal of Bone and Joint Surgery, "The Use of a Dynamometer with Adjustable Handle Spacings", pp. 820–824.
A Microcomputer Controlled Hand Assessment System Used for Clinical Measurement, by A. R. Joes, A. Unsworth and I. Haslock, pp. 191–198, 1985.
T.K.K. Psychological & Physiological Apparatus, "Muscle Measurement", by Takei & Company, Ltd., p. 48, 1986.

Primary Examiner—Richard E. Chilcot, Jr.
Assistant Examiner—Elizabeth L. Dougherty
Attorney, Agent, or Firm—Westman, Champlin & Kelly

[57] ABSTRACT

A digit grip sensor for measuring the grip strength of the human hand. The digit grip sensor comprises a post support having a first and a second sensor therein. A first post extends through the first sensor and a second post extends through the second sensor. A crossbar spaced from the post support extends between the first post and the second post. Each sensor has a plurality of strain gages mounted thereon for measuring the deflection of the sensor. The crossbar can have a plurality of individual digit sensors mounted thereon for measuring the contributions of each finger to the grip force. The crossbar and the individual digit sensors can be adjusted for various hand and finger sizes.

19 Claims, 5 Drawing Sheets

DIGIT GRIP SENSOR

BACKGROUND OF THE INVENTION

The present invention relates to the measurement of the grip or grasp strength of the human hand and, in particular, to an apparatus that measures the grip strength of the human hand. Such an apparatus has numerous benefits including medical uses such as the diagnosis of motor function weaknesses in the hand and ergonomic uses such as aiding in the design of tools that are more responsive to the forces applied by a hand.

Current similar devices for the measurement of grip strength generally use hydraulics to sense the magnitude of the force applied. A problem with this method of sensing force is that the hydraulic fluid will absorb some of the force, resulting in an inaccurate measurement. In addition, some new electromechanical devices use handles that deflect substantially when placed under a large grip load. The result is that these devices also absorb some force and are therefore not isometric in the measurement of grip strength.

During the gripping of the device, more than one grip load is simultaneously applied to the device. The ability to accurately distinguish between the primary load and cross loads is extremely important to a precise evaluation of grip strength. A problem with the current devices for measuring grip strength is that they do not distinguish between the various components of the grip load. The result is a decrease in the accuracy of their measurement.

In addition, currently used devices are not capable of determining the location of the resultant force acting on the device and do not measure the contribution of each digit to the total grip load.

SUMMARY OF THE INVENTION

The present invention provides an apparatus that is capable of measuring the grip strength of a human hand. The apparatus as disclosed comprises a post support containing a first sensor and a second sensor for measuring the grip forces of the hand and two posts for transmitting the grip forces from a crossbar to the first and second sensors. The post support, the first post and the second post form a rigid body that is substantially isometric, resulting in extremely accurate measurements.

The first sensor is located in a first end of the post support and the second sensor is located in a second end. The first post extends through the center of the first sensor and the second post extends through the center of the second sensor. The crossbar extends between the first post and the second post.

Each sensor comprises four rectangular shear flexures radially extending from a central member and having a plurality of strain guges mounted thereon. The central member and shear flexures deflect slightly when subjected to a grip force, causing some strain gages to stretch and others to contract. The strain gages provide signals that are sent through lead wires to be processed into usable data.

An upper grip is attached to an upper side of the crossbar and a lower grip is attached to a lower side of the post support so that a human hand can comfortably grip the digit grip sensor by placing the fingers on the upper grip and the thumb on the lower grip. The apparatus can be adapted to measure the individual contributions of each finger to the total grip force.

DETAILED DESCRIPTION OF THE PREFERRED EMBODIMENTS

Figure 1:
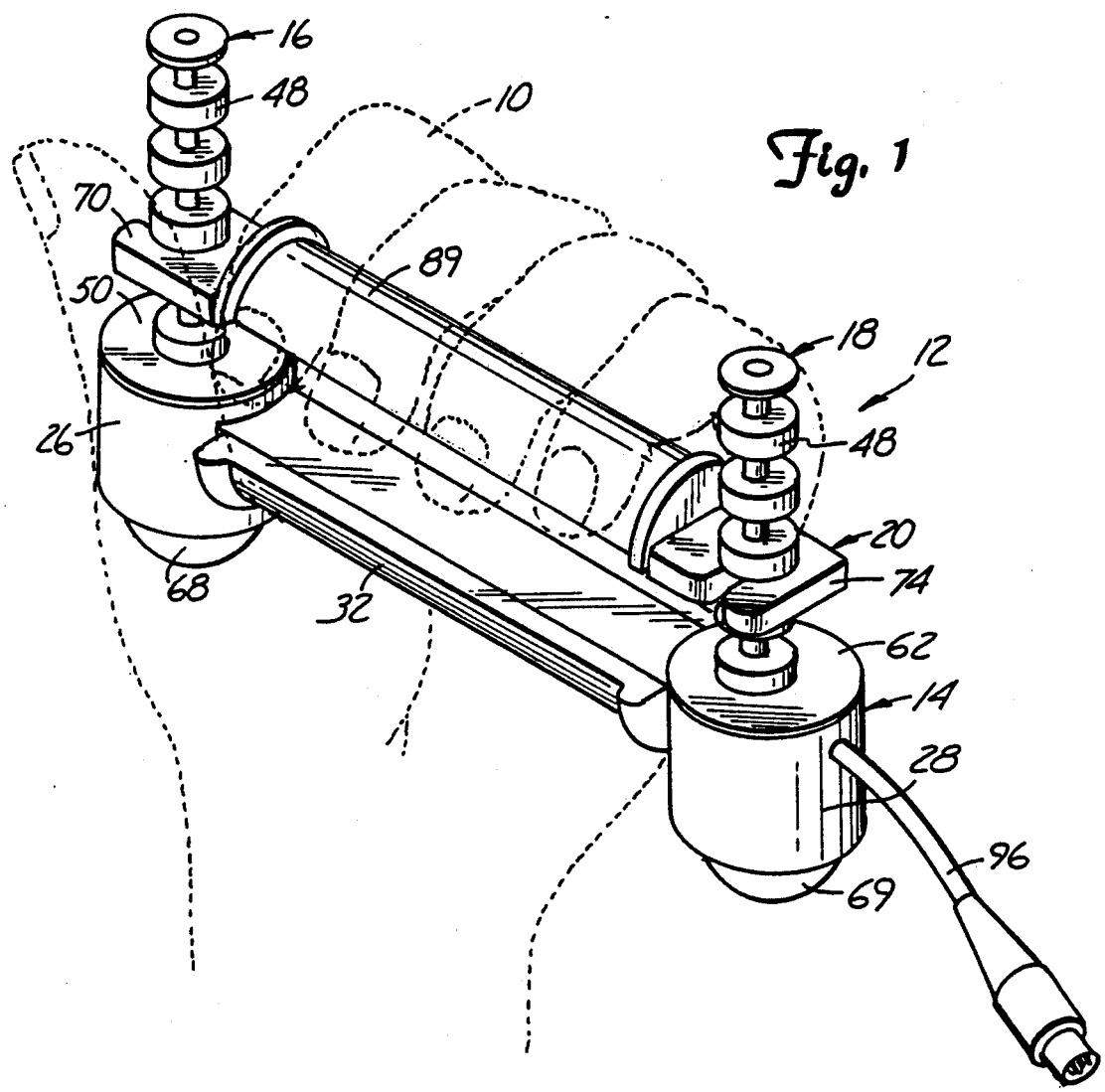
FIG. 1 is a perspective view of a hand gripping the apparatus of the present invention.

A human hand 10 grasping a digit grip sensor 12 of the present invention is shown in FIG. 1. The digit grip sensor 12, shown in more detail in FIG. 2, comprises a post support 14, a first post 16, a second post 18 and a crossbar 20. A first shear sensor 22 and a second shear sensor 24 are contained in the post support 14.

The post support 14 comprises a first end tube 26 and a second end tube 28 having circular cross sections and a connecting member 30 having the general shape of an elongated rectangular block extending between them. A lower grip 32 is removably attached to the connecting member 30. The post support 14 is fabricated from a rigid, lightweight material such as aluminum.

Figure 4:
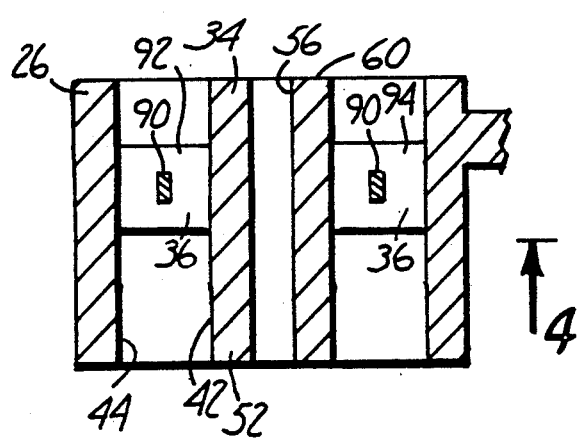
FIG. 4 is a sectional view of a portion of the post support taken along the line 4—4 of FIG. 3.
Figure 3:
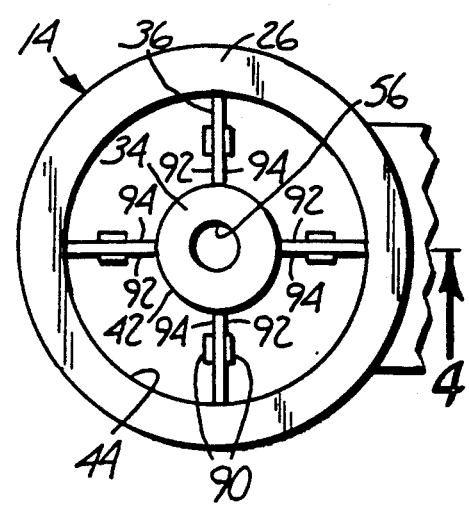
FIG. 3 is a top view of a portion of the post support of the present invention containing a shear sensor.

The first shear sensor 22, shown in FIGS. 3 and 4, is structurally integrated in the post support 14 and comprises a hollow cylinder 34 concentric with the first end tube 26 and four rectangular shear flexures 36. Each flexure 36 radially extends from an outer cylindrical surface 42 of the hollow cylinder 34 to an inner cylindrical surface 44 of the first end tube 26 and is perpendicular to the adjacent flexures 36. The second shear sensor 24 is also structurally integrated in the post support 14 and is identical to the first shear sensor 22. Each rectangular flexure 36 radially extends from the outer cylindrical surface 42 of the hollow cylinder 34 to an inner cylindrical surface 46 of the second end tube 28.

Both the first post 16 and the second post 18, which are fabricated from a rigid, lightweight material such as aluminum, have a plurality of ribs 48 evenly spaced along a portion of their length. The first post 16 extends through a hole 49 in the center of a first end tube cover 50 and through the hollow cylinder 34 of the first shear sensor 22 so that a threaded first end 51 protrudes from a first end 52 of the hollow cylinder 34. An outer cylindrical surface 54 of the first post 16 tightly contacts an inner cylindrical surface 56 of the hollow cylinder 34 and a bottom surface 58 of a first of the ribs 48 tightly contacts a second end 60 of the hollow cylinder 34.

The second post 18 extends through a hole 61 in the center of a second end tube cover 62 and through the hollow cylinder 34 of the second shear sensor 24 so that a threaded first end 63 protrudes from the first end 52 of the hollow cylinder 34. An outer cylindrical surface 64 of the second post 18 tightly contacts the inner cylindrical surface 56 of the hollow cylinder 34 and a bottom surface 65 of a first of the ribs 48 tightly contacts the second end 60 of the hollow cylinder 34.

Two nuts 66 are screwed onto the first end 51 of the first post 16 and two nuts 67 are tightly screwed onto the first end 63 of the second post 18 to rigidly hold the posts 16,18 in place. The tight fit within the hollow cylinder 34 prevents any movement of the first post 16 relative to the first shear sensor 22 or the second post 18 relative to the second shear sensor 24. A first bottom cap 68 is screwed onto the first end 51 of the first post 16 and a second bottom cap 69 is screwed onto the first end 63 of the second post 18.

The crossbar 20 has the general shape of an elongated rectangular block having a first extension 70 at a first end 72 and a second extension 74 at a second end 76. An end slot 78 in an end surface 80 of the first extension 70 receives the first post 16 at a position between two of the ribs 48 such that a lower surface 82 of the first extension 70 rests on a facing surface of the adjacent rib 48. A side slot 84 in a side surface 86 of the second extension 74 receives the second post 18 at a position between two of the ribs 48 such that a lower surface 88 of the second extension 74 rests on a facing surface of the adjacent rib 48. The first post 16 snaps into the end slot 78 and the second post 18 snaps into the side slot 84. An upper grip 89 is removably attached to the crossbar 20.

The thickness of the first and second extensions 70,74 relative to the distance between the ribs 48 and the width of the end and side slots 78,84 relative to the width of the first and second posts 16,18 are such that the crossbar 20 is loosely held in place between the first post 16 and the second post 18. The result is that the crossbar 20 is structurally free or floating with respect to the first and second posts 16,18.

Figure 2:
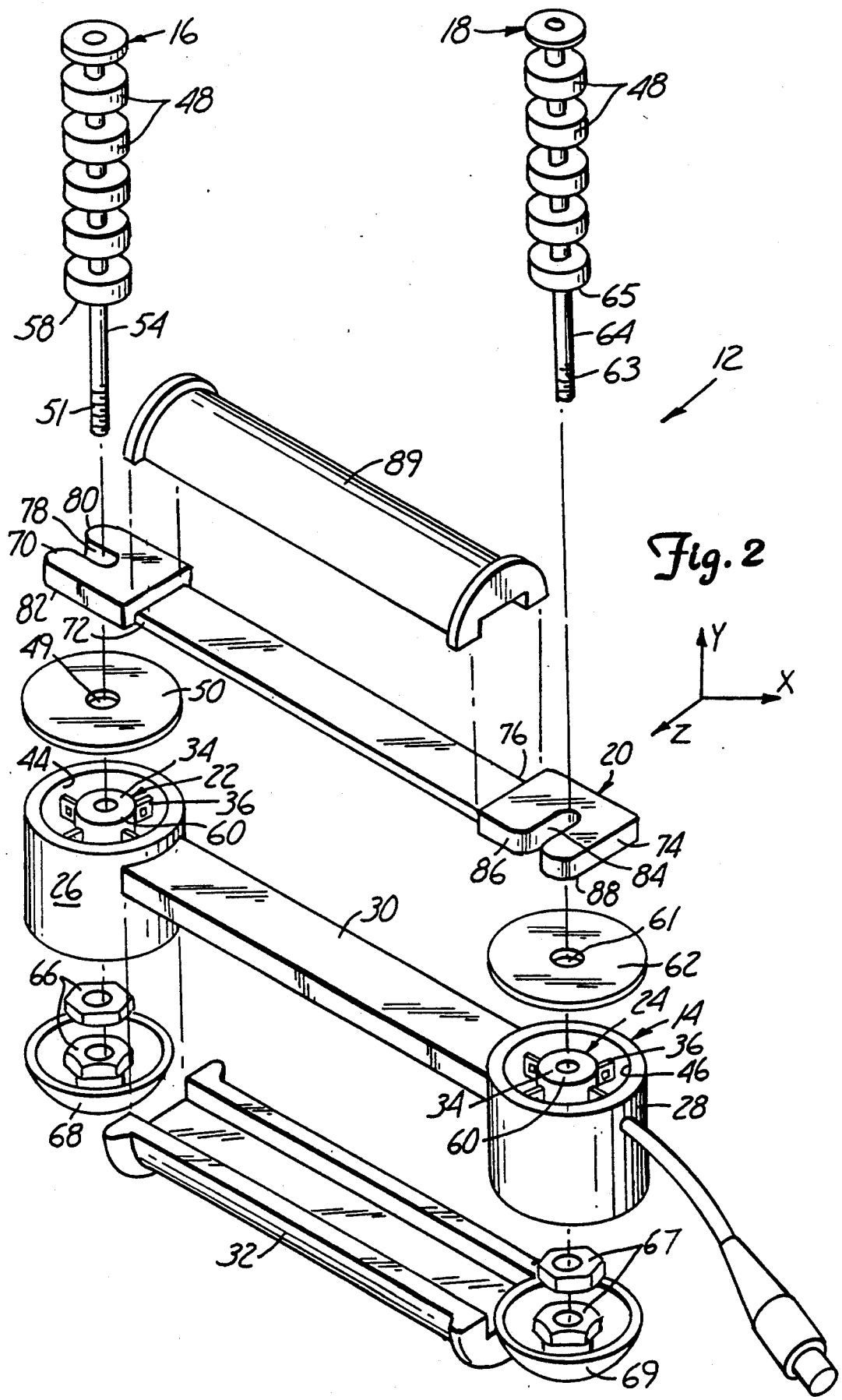
FIG. 2 is an exploded perspective view of the apparatus of the present invention.

The directions of the three orthogonal components of the forces acting on the crossbar 20 are represented by the directional axes X, Y, and Z shown in FIG. 2. Because the crossbar 20 is structurally floating, it is able to transmit the Y component of the forces acting on it while substantially eliminating the transmission of the X and Z components.

The rigidity of the first post 16, the second post 18, the post support 14 and the crossbar 20, creates an isometric structure that minimizes the deflection that occurs when the structure is subjected to large loads. Therefore, the force exerted on the crossbar 20 will be substantially equivalent to the sum of the forces acting on the first sensor 22 and the second sensor 24 permitting the digit grip sensor 12 to provide an extremely accurate measurement of the force exerted. In addition, the use of two independent shear sensors 22,24 enables the digit grip sensor 12 to accurately determine the position of the resultant force acting on the crossbar 20 through the use of principles known in the art.

A strain gage 90 is mounted on each of a first surface 92 and a second surface 94 of each rectangular shear flexure 36 of the first shear sensor 22 and the second shear sensor 24. The strain gages 90, shown in FIGS. 3 and 4, are mounted at a 45° angle relative to the hollow cylinder 34. When a force is transmitted through either the first post 16 or the second post 18, the hollow cylinder 34 and rectangular flexures 36 of the corresponding sensor 22,24 will deflect slightly (less than 0.00001 inches) in the direction of the Y axis. The strain gages 90 mounted on the first surface 92 of each rectangular flexure 36 will stretch causing a tension while the strain gauges 90 mounted on the second surface 94 of each rectangular flexure 36 will contract causing a compression.

The tension and compression is converted into electrical signals by the strain gauges 90 which are electrically connected in a Wheatstone Bridge configuration in a manner that intrinsically minimizes the effect of cross-talk due to any X and Z components of the forces while enabling the measurement of the Y component of the forces. A plurality of wires 96 electrically connect the strain gages to an apparatus that is capable of calculating the forces on the crossbar 20 from the electrical signals sent by the strain gages 90.

Figure 5:
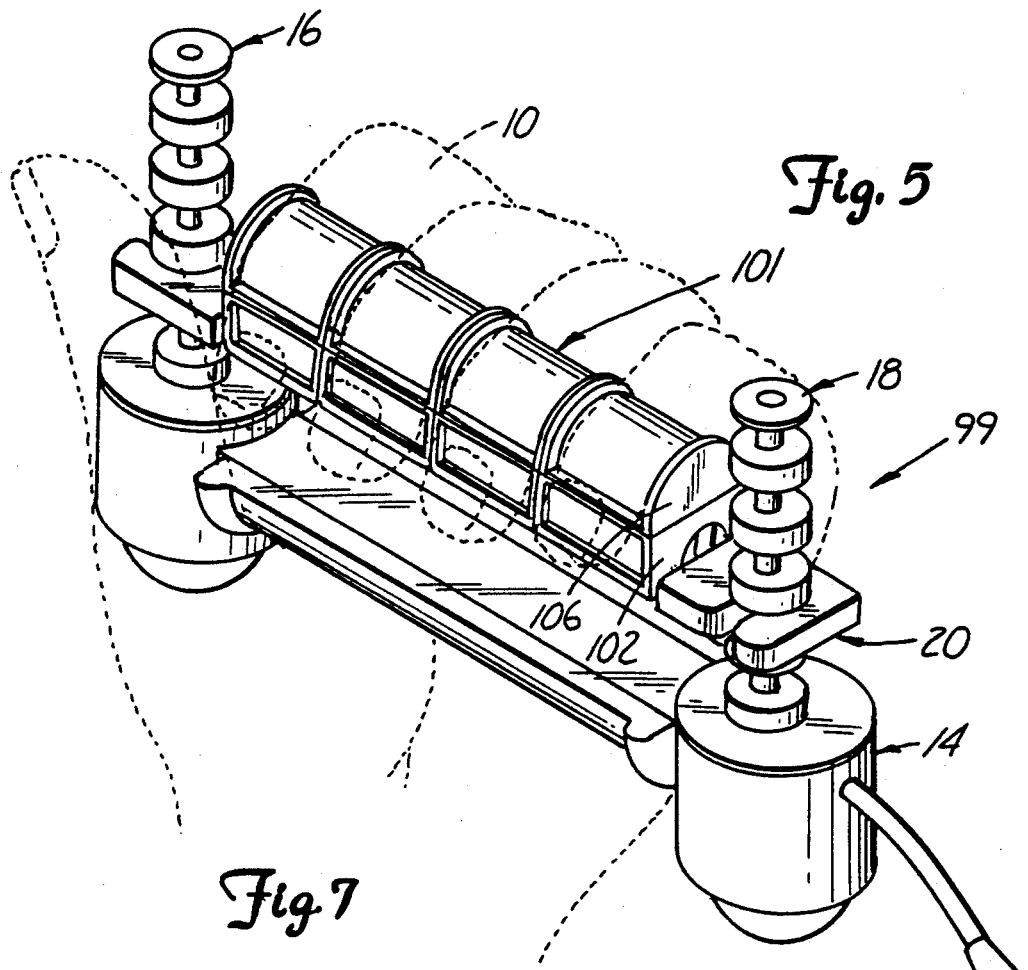
FIG. 5 is a perspective view of a hand gripping a modified form of the apparatus of the present invention.
Figure 6:
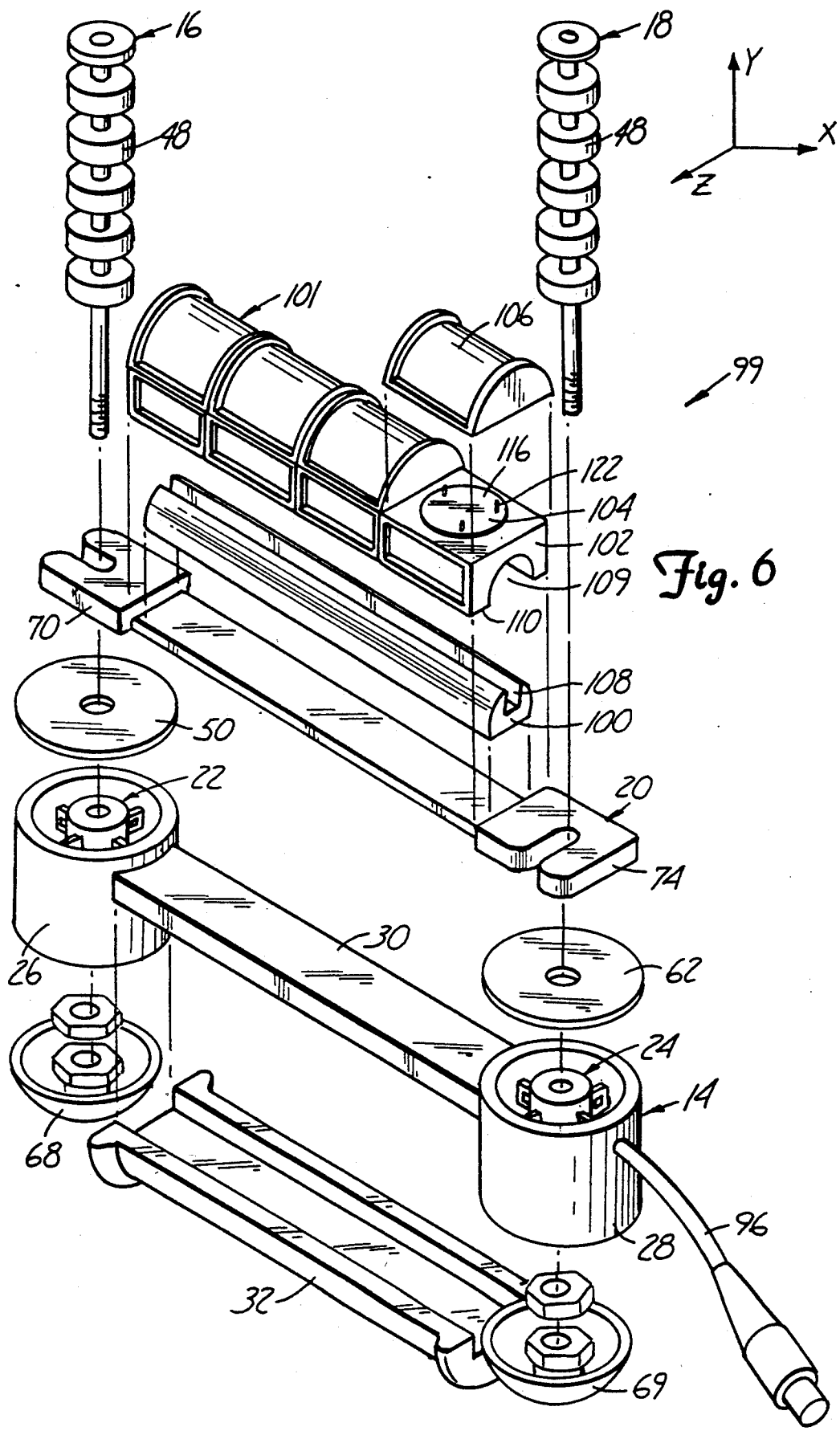
FIG. 6 is an exploded perspective view of a modified form of the apparatus of the present invention.

In a first alternative embodiment of the present invention, shown in FIGS. 5 and 6, the crossbar 20 of a digit grip sensor 99 supports a circular shaft 100 having four digit sensor assemblies 101 thereon. Each digit sensor assembly 101 comprises a sensor mount 102, a digit sensor 104 and a finger pad 106. The remainder of the digit grip sensor 99 is similar to that described in the first embodiment.

The circular shaft 100 is mounted on the crossbar 20 between the first extension 70 and the second extension 74 and has a channel 108 extending along its length. The shaft 100 is inserted into a groove 109 in a first side 110 of each sensor mount 102 so that the sensor mount 102 is capable of sliding along the length of the shaft 100 and rotating up to 30° in either direction about the shaft 100. Each sensor mount 102 has a generally circular recess 111 in a second side 112 having three equally spaced bores 113 around its periphery.

The movement of the sensor mounts 102 on the shaft 100 allows the adjustment of the digit sensors 104 for different size hands. In addition, the movement of the sensor mounts 102 greatly reduces the transmission of the X and Z components of the force to the digit sensors 104, permitting a more accurate measurement of the Y component of the force.

Figure 7:
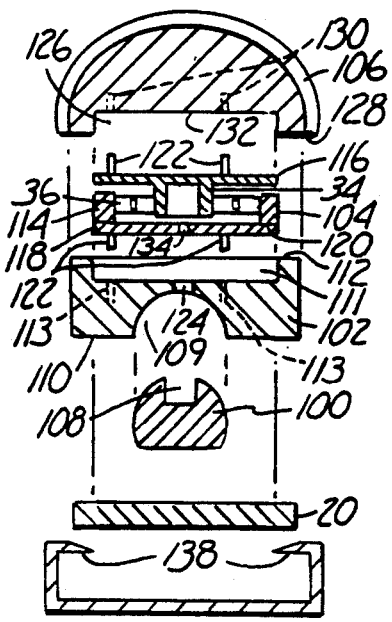
FIG. 7 is a side view of the digit sensor assembly of the present invention.

Each digit sensor 104, shown in FIG. 7, is similar to the first shear sensor 22 and the second shear sensor 24 except that the end of each rectangular shear flexure 36 furthest from the hollow cylinder 34 is attached to an outer ring 114. A top cover 116 having the general shape of a disk comes into contact with the second end 60 of the hollow cylinder 34 and a bottom cover 118 having the general shape of a disk comes into contact with a first end 120 of the outer ring 114.

Both the top cover 116 and the bottom cover 118 have three studs 122 equally spaced along the periphery of an outer surface. The studs 122 on the bottom cover 118 are inserted into the bores 113 in the recess 111 of the sensor mount 102 so that the bottom cover 118 rests on a bottom surface 124 of the recess 111. The finger pad 106 has a recess 126 in a first side 128 having three equally spaced bores 130 around its periphery. The studs 122 on the top cover 116 are inserted into the bores 130 so that a top surface 132 of the recess 126 rests on the top cover 116. An opening 134 in the center of each bottom cover 118 permits wires to extend from the digit sensors 104, through the sensor mounts 102, into the channel 108.

A plurality of snaps 136 can be attached to the crossbar 20 so that tabs 138 are placed between the crossbar 20 and the digit sensor mounts 102. This prevents the digit sensor mounts 102 from rotating about the shaft 100 without preventing them from sliding along the axis of the shaft 100. When the digit sensor mounts 102 are held in this manner, all three components of the forces acting on the sensor are optimized.

Figure 8:
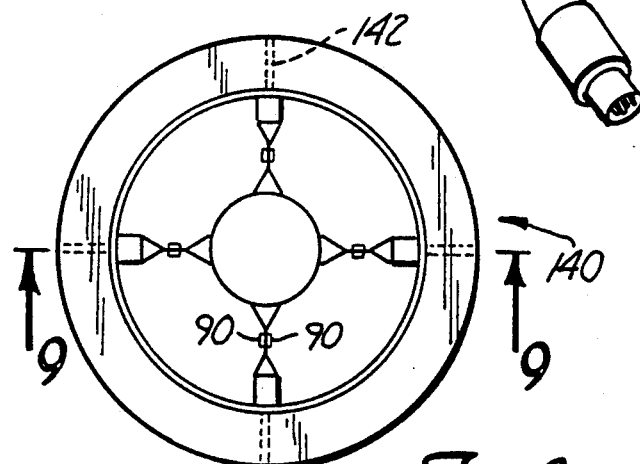
FIG. 8 is a top view of a modified form of the shear sensor of the present invention.
Figure 9:
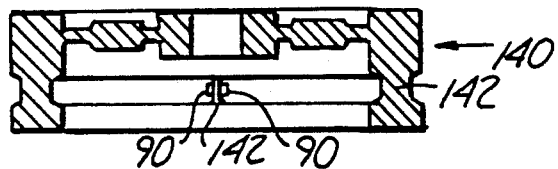
FIG. 9 is a sectional view of a modified form of the shear sensor taken along the line 9—9 of FIG. 8.

A three-component digit sensor 140, shown in FIGS. 8 and 9, can be mounted in each of the digit sensor mounts 102 in the same manner as the digit sensor 104 to measure each of the X, Y, and Z components of the force applied by the fingers. The three-component digit sensor 140 has a hollow cylinder 34 and four rectangular shear flexures 36 similar to those of the digit sensor 104 to measure the Y component of the forces acting on it. However, the outer ring 114 of the three-component digit sensor 140 is supported above a base ring 141 by four flexure supports 142. Each flexure support 142 has a strain gage 90 mounted on each side thereof to measure the X and Z components of the forces acting on the sensor 140.

Figure 10:
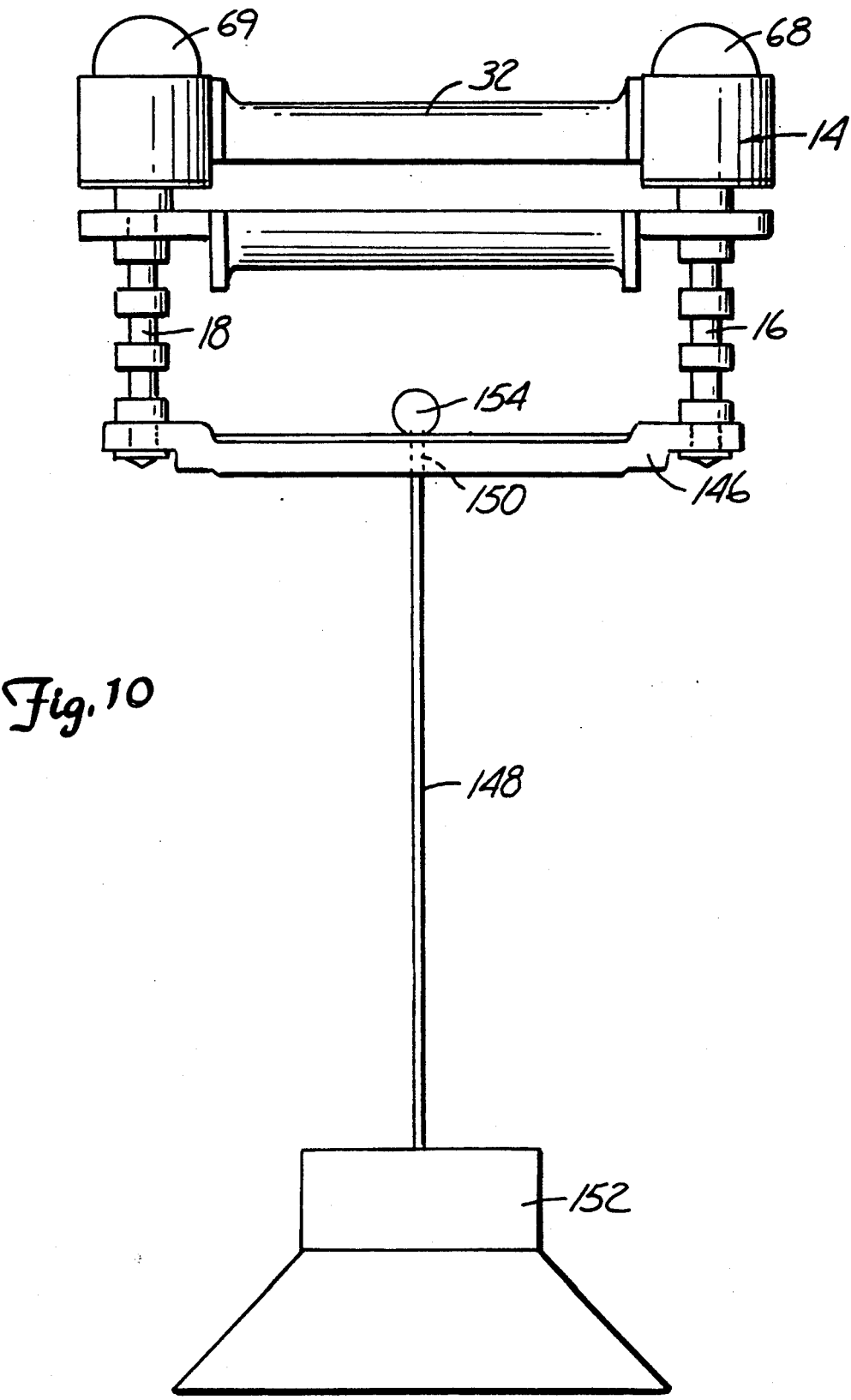
FIG. 10 is a front elevation view of the apparatus of the present invention configured to determine the lift strength of a human hand.

The first shear sensor 22 and the second shear sensor 24 are both equally linear in the positive and negative Y directions. This allows the digit grip sensor 12 to be configured to measure the lift and pull capacities of the hand. In such a configuration, shown in FIG. 10, a second crossbar 146 having a construction similar to that of the crossbar 20 extends between the first post 16 and the second post 18. A wire 148 extends through a hole 150 in the second crossbar 146 and supports a weight 152 at a first end. A ball 154 is attached to the wire 148 at a second end and contacts the second crossbar 146 so that the second crossbar 146 will support the weight 152.

To measure the lift strength, the digit grip sensor 12 is held with the ends of the first and second posts 16,18 furthest from the post support 14 facing the ground. The lower grip 32 is moved to a side of the connecting member 30 facing the second crossbar 146 and the digit grip sensor 12 is lifted with the fingers gripping the lower grip 32. A similar test for pull strength can be performed with the first end of the wire 148 attached to a fixed object instead of the weight 152.

The same lift and pull tests can be performed with the digit grip sensor 99 of the first alternative embodiment in the same manner as described above except that the crossbar 20 remains in place between the two ribs 48 closest to the post support 14. To measure the lift capacity, the digit grip sensor 99 is lifted with the fingers gripping the finger pads 106 of the digit sensor assemblies 101.

In the present invention, one of the strain gages 90 is described as being mounted on each of the first side 92 and the second side 94 of each rectangular shear flexure 36. However, two strain gages 90 can be mounted on the first side 92 of each rectangular flexure 36 with none mounted on the second side 94 or, two strain gages 90 can be mounted on the second side 94 of each rectangular flexure 36 with none mounted on the first side 92. In each situation, the two strain gages 90 are mounted on the rectangular flexure 36 so that each forms a 45 degree angle with the hollow cylinder 34 and is perpendicular to the other so that one strain gage 90 stretches and the other strain gage 90 contracts when the hollow cylinder 34 is deflected.

Although the first and second shear sensors 22,24 were described as being integral with the post support 14, they can be integral with the first and second posts 16,18 respectively or can be integral with both the posts and the post support 14. Finally, the digit grip sensor 12 can be adjusted for use with hands of different sizes by removing the crossbar 20 from its place and sliding both the end slot 78 and the side slot 84 between a different pair of ribs 48.

Although the present invention has been described with reference to preferred embodiments, workers skilled in the art will recognize that changes may be made in form and detail without departing from the spirit and scope of the invention.

What is claimed is:

1. An apparatus for measuring the grip force exerted by a human hand, the apparatus comprising:
   a post support a first load sensor and a second load sensor adjacent opposite ends thereof;
   a first post substantially rigidly attached to the first sensor;
   a crossbar extending between the first post and the second post and spaced from the post support, the post support, first post, second post and crossbar forming a structure that can be gripped by a human hand and wherein gripping forces load the first and second posts substantially in compression and the first and second sensors substantially in shear; and
   sensing means for sensing shear loading on the first and second sensors.

2. The apparatus of claim 1 wherein the first sensor comprises a hollow cylinder having a plurality of generally rectangular shear flexures radially extending from an outer cylindrical surface thereof and the second sensor comprises a hollow cylinder having a plurality of generally rectangular shear flexures radially extending from an outer cylindrical surface thereof.

3. The apparatus of claim 2 wherein the sensing means is a plurality of strain gages mounted on the rectangular shear flexures of both the first sensor and the second sensor.

4. The apparatus of claim 2 wherein the first sensor and the second sensor are structurally integrated with the post support.

5. The apparatus of claim 4 wherein the first post extends through the hollow cylinder of the first sensor and the second post extends through the hollow cylinder of the second sensor.

6. The apparatus of claim 5 wherein a first end of the first post and a first end of the second post are threaded and the first and second posts are held in place through the use of a plurality of nuts.

7. The apparatus of claim wherein the post support, the first post, the second post and the crossbar form a substantially rigid structure.

8. The apparatus of claim 1 and an upper grip removably attached to an upper surface of the crossbar.

9. The apparatus of claim 1 and a lower grip removably attached to a lower surface of the post support.

10. The apparatus of claim 1 and a mounting shaft extending along the length of the crossbar.

11. The apparatus of claim 10 and four sensing means rotatably attached to the mounting shaft for measuring the force exerted by each finger.

12. The apparatus of claim 11 wherein the sensing means slide along the length of the mounting shaft.

13. The apparatus of claim 11 wherein the sensing means comprise a sensor housing having an upper half and a lower half and a digit sensor mounted therein.

14. The apparatus of claim 13 wherein the digit sensor comprises a hollow cylinder having a plurality of generally rectangular shear flexures radially extending from an outer cylindrical surface thereof.

15. The apparatus of claim 1 and support means extending between the first post and the second post for supporting a first end of a wire having a weight attached at a second end.

16. An apparatus for measuring the grip force exerted by a human hand, the apparatus comprising;
   a post support comprising an elongated beam;
   a first post substantially rigidly attached to the post support at one end thereof;
   a second post substantially rigidly attached to the post support at a second end thereof;
   a crossbar extending between the first post and the second post and spaced from the post support, the post support, first post, second post and crossbar forming a structure which can be gripped and wherein grip force loads tends to urge the post support and crossbar together; and
   sensing means mounted on the crossbar for measuring grip force exerted on the structure, said sensing means being mounted to slide along the length of and rotate about the crossbar.

17. The apparatus of claim 16 wherein there are four sensing means, and each comprises a sensor housing having an upper half and a lower half and a digit sensor mounted within the sensor housing.

18. The apparatus of claim 17 wherein the digit sensor comprises a hollow cylinder having a plurality of rectangular shear flexures radially extending from an outer cylindrical surface thereof to an outer ring.

19. An apparatus for measuring the grip force exerted by a human hand, the apparatus comprising;
   a post support comprising an elongated beam;
   a first post substantially rigidly attached to the post support at one end thereof;
   a second post substantially rigidly attached to the post support at a second end thereof;
   a crossbar extending between the first post and the second post and spaced from the post support, the post support, first post, second post and crossbar forming a structure that loads the first and second posts substantially in compression posts subjected to grip force loads; and
   sensors at opposite ends of the post support loaded in shear from compression loading on the posts for measuring components of grip force exerted at the structure at each post.

* * * * *

UNITED STATES PATENT AND TRADEMARK OFFICE
CERTIFICATE OF CORRECTION

PATENT NO. : 5,317,916
DATED : June 7, 1994
INVENTOR(S) : Nebojsa Kovacevic

It is certified that error appears in the above-indentified patent and that said Letters Patent is hereby corrected as shown below:

Column 6, line 46, after "claim" insert --1--.

Signed and Sealed this

Eighteenth Day of October, 1994

Attest:

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 5,317,916
DATED : June 7, 1994
INVENTOR(S) : Nebojsa Kovacevic

It is certified that error appears in the above-indentified patent and that said Letters Patent is hereby corrected as shown below:

```
Column 6, line 14, after sensor; insert --a
second post substantially rigidly attached to the
second sensor;--
```

Signed and Sealed this

Twenty-seventh Day of June, 1995

Attest:

BRUCE LEHMAN

Attesting Officer     Commissioner of Patents and Trademarks